(12) United States Patent
Chan et al.

(10) Patent No.: US 7,361,773 B2
(45) Date of Patent: *Apr. 22, 2008

(54) PREPARATION OF N1-(2'-PYRIDYL)-1,2-PROPANEDIAMINE SULFAMIC ACID AND ITS USE IN THE SYNTHESIS OF BIOLOGICALLY ACTIVE PIPERAZINES

(75) Inventors: Anita Wai-Yin Chan, Fort Lee, NJ (US); Gregg Brian Feigelson, Chester, NY (US); Joseph Zeldis, New City, NY (US); Ivo Ladislav Jirkovsky, Waitsfield, VT (US)

(73) Assignee: Wyeth, Madison, NJ (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/919,099

(22) Filed: Aug. 16, 2004

(65) Prior Publication Data

US 2005/0070709 A1    Mar. 31, 2005

Related U.S. Application Data

(63) Continuation-in-part of application No. 10/385,337, filed on Mar. 10, 2003, now Pat. No. 6,784,294.

(60) Provisional application No. 60/363,457, filed on Mar. 12, 2002.

(51) Int. Cl.
    *C07D 319/14*    (2006.01)
(52) U.S. Cl. .................................... 549/366
(58) Field of Classification Search ............... 549/366, 549/297, 296
    See application file for complete search history.

(56) References Cited

U.S. PATENT DOCUMENTS

| | | | |
|---|---|---|---|
| 5,424,313 A | 6/1995 | Hertog et al. | |
| 5,889,010 A | 3/1999 | Faraci et al. | |
| 6,127,357 A | 10/2000 | Cliffe et al. | |
| 6,271,234 B1 | 8/2001 | Leonardi et al. | |
| 6,713,626 B2 * | 3/2004 | Feigelson et al. | 544/360 |
| 6,784,294 B2 * | 8/2004 | Chan et al. | 544/360 |
| 7,019,137 B2 | 3/2006 | Jirkovsky et al. | |
| 7,091,349 B2 | 8/2006 | Feigelson et al. | |
| 2004/0230056 A1 | 11/2004 | Feigelson et al. | |

FOREIGN PATENT DOCUMENTS

| | | |
|---|---|---|
| JP | 01125357 A2 | 5/1989 |
| WO | WO-9322303 | 11/1993 |
| WO | WO 94/24115 | 10/1994 |
| WO | WO 95/33725 | 12/1995 |
| WO | WO 95/33743 | 12/1995 |
| WO | WO-9601656 | 1/1996 |
| WO | WO 97/03982 | 2/1997 |
| WO | WO 97/37655 | 10/1997 |
| WO | WO-0244142 | 6/2002 |
| WO | WO-03/078417 | 9/2003 |

OTHER PUBLICATIONS

Kagayaki Natsuka et al., J. Med. Chem., 1987, 1779-1787, 30.
Frank Kerrigan et al., Tetrahedron Letters, 1998, 2219-2222, 39.
Sheryl J. Hays, J. Labelled Compounds and Radiopharmaceuticals, 1986, 351, 24(4).
Jean-Louis Peglion et al., J. Med. Chem., 1995, 4044-4055, 38.
Shawn J. Stachel et al., Tetrahedron Letters, 1999, 5811-5812, 40.
Julian M.C. Golec et al., Bioorganic & Medicinal Chemistry Letters, 1997, 2181-2186, 7(17).
Dan Muller, J. Org. Chem., 1997, 411-416, 62.
G. Mark Taylor et al., Tetrahedron Letters, 1996, 1297-1300, 37(8).
Database Crossfire Beilstein, Reg. No. 3915193.
Database Crossfire Beilstein, Reg. No. 1512459.
Zoltan Zubovics, Eur. J. Med. Chem., 1986, 370-378, 21(5).
G. Cignarella et al., Il Farmaco—Ed. Sc., 1976, p. 194, 196, v. 31.
Lee T. Boulton, J. Chem. Soc., Perkin Trans. 1, 1999, 1421-1429.
G. Cignarella, Il Farmaco—Ed. Sc., 1976, 194-200, 31(3).
Ulrike Burkard et al., Chem. Ber., 1986, 1594-1612, 119.
Wincenty Kwapiszewski et al., Acat Pol. Pharm., 1999, 41-47, 56(1) (Abstract).
Michimasa Izumi et al., Chem. and Pharm. Bull. (Japan), 1954, 275-279, 2(3).
Isao Aiko et al., Chem. and Pharm. Bull. (Japan), 1957, 487-488, 5(5).
Syed M. Quadri et al., Bioorganic & Medicinal Chemistry Letters, 1992, 1661-1664, 2(12).
Robert V. Hoffman et al., Tetrahedron Letters, 1990, 2953-2956, 31(21).
Sandrine Marchais et al., Bioorganic & Medicinal Chemistry, 2001, 695-702, 9.
European Search Report, issued May 25, 2007, for EP07007755.7-1211.

* cited by examiner

*Primary Examiner*—Thomas McKenzie
*Assistant Examiner*—Raymond Covington
(74) *Attorney, Agent, or Firm*—Wilmer Cutler Pickering Hale and Dorr LLP

(57) ABSTRACT

A process for making a compound of the formula comprising dialkylating a benzodioxane aniline

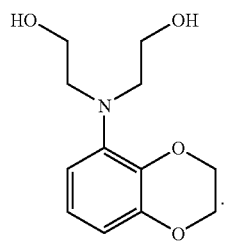

7 Claims, No Drawings

PREPARATION OF N1-(2'-PYRIDYL)-1,2-PROPANEDIAMINE SULFAMIC ACID AND ITS USE IN THE SYNTHESIS OF BIOLOGICALLY ACTIVE PIPERAZINES

This application is a continuation-in-part of application Ser. No. 10/385,337, filed on Mar. 10, 2003, which claims priority from provisional application Ser. No. 60/363,457, filed on Mar. 12, 2002, the entire disclosure of which is hereby incorporated by reference.

FIELD OF THE INVENTION

This invention relates to the field of processes for preparing N-aryl piperazines and intermediates therefor.

BACKGROUND OF THE INVENTION

Piperazines of formula A

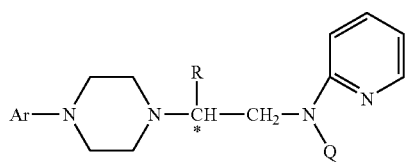

wherein R is a lower alkyl, Ar is an unsubstituted or substituted aryl or heteroaryl, and Q is a hydrogen, CO-(lower) alkyl, CO-cycloaklyl, or CO-aryl, and * indicates a chiral center are potent $5HT_{1A}$ receptor binding agents. U.S. Pat. No. 6,127,357 teaches piperazine derivatives that are useful in the treatment of Central Nervous System (CNS) disorders. Enantiomers of such piperazines can display different binding abilities to $5HT_{1A}$ receptors. Therefore, their potency, selectivity, and metabolic effects may be different. WO 9703982 teaches that certain enantiomers of such piperazines display improved $5HT_{1A}$ binding affinity and bioavailability. Therefore, an efficient, operationally facile, inexpensive and safe alternative process for making the optically preferred piperazines is desirable.

WO 9533725 teaches a method for synthesizing some chiral piperazines of formula A by alkylation of the corresponding 1-aryl-piperazine with enantiomerically pure 2-(5-methyl-2,2-dioxido-1,2,3-oxathiazolidin-3-yl)pyridine. WO 9533725 also teaches nucleophilic ring openings of sulfamidates with 1-aryl-piperazine and opening with various primary and secondary amines is known form L. T. Boulton, J. Chem. Soc., Perkin Trans. 1, 1999, 1421-1429.

WO 97/37655 and Cignarella et al., Farmaco Ed. Sci.; 31; 1976; 194, 196 discuss preparation and reaction of N1-(2'pyridyl)-1,2-propane-diamine.

SUMMARY OF THE INVENTION

The present invention is a process for making an N1-(2'-pyridyl)-1,2-alkanediamine sulfamic acid of formula II comprising reacting a compound of formula I with $NH_2R'$

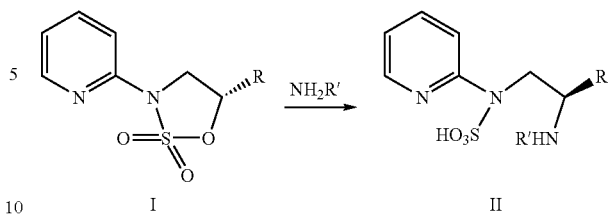

wherein R is selected form the group consisting of $C_1$-$C_3$ alkyl, and R' is H, $C_1$-$C_6$ alkyl, $C_3$-$C_7$ cycloalkyl, $C_2$-$C_7$ acyl, $C_5$-$C_{10}$ aryl $C_6$-$C_{11}$ aroyl, $(C_3$-$C_7)$cycloalkyl($C_1$-$C_6$)alkyl, di-$(C_3$-$C_7)$cycloalkyl -$(C_1$-$C_6)$alkyl, $(C_5$-$C_{10})$aryl($C_1$-$C_6)$ alkyl, and di-$(C_5$-$C_{10})$aryl-$(C_1$-$C_6)$alkyl. The invention further comprises the compound of formula II and optical isomers thereof.

The invention also includes processes that comprise one or more of the following reaction steps:

The compound of formula II may be hydrogenated to convert R' to H, if it is not already H, and then hydrolyzed using an acid to form the compound of formula III

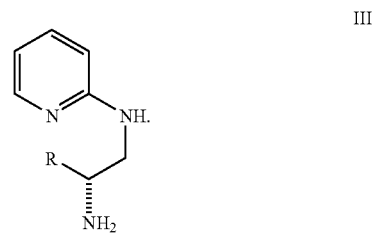

Either the compound of formula II where R'=H, or the compound of formula III, may be reacted with the compound of formula IV to form the compound of formula V

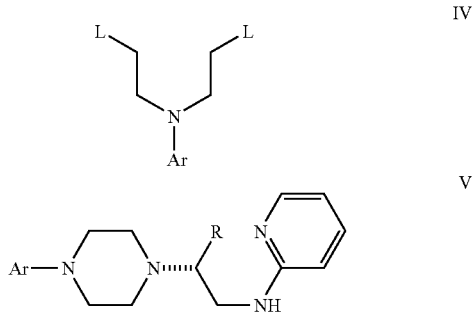

wherein Ar is a dihydrobenzodioxinyl or benzodioxinyl, or phenyl optionally substituted with up to three substituents independently selected from halogen, methoxy, halomethyl, dihalomethyl and trihalomethyl, and L is a suitable group such as halo (especially chloro or bromo), tosylate, mesylate or p-bromophenyl-sulfonyloxy.

The compound of formula V may be treated an with aroyl compound selected from aroyl chloride, aroyl bromide and aroyl anhydride, in the presence of a base, to form a compound of formula VI

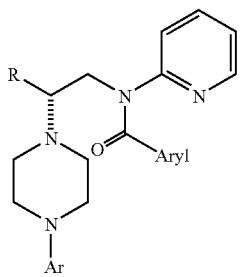

wherein Aryl represents a $C_6$-$C_{12}$ aromatic group optionally substituted with up to three substituents independently selected from the group consisting of halogen atoms, alkyl, alkoxy, alkoxycarbonyl, nitro, amino, alkylamino, dialkylamino, haloalkyl, dihaloalkyl, trihaloalkyl, nitrile and amido substituents each having no more than six carbon atoms.

It is an object of the present invention to provide a novel intermediate compound of formula II useful in preparing N-aryl piperazines.

It is a further object of this invention to provide a novel process for making N-aryl piperazines and intermediates therefor.

It is another object of the invention to provide a novel process for making a compound of formula II.

Other objects and advantages of the present invention will be apparent to those skilled in the art from consideration of the detailed description of the invention provided herein, and from the appended claims.

DETAILED DESCRIPTION OF THE PREFERRED EMBODIMENTS

A preferred embodiment of this invention is a new process for preparing N-aryl piperazines using N1-(2'-pyridyl)-1,2-propanediamine sulfamic acid, particularly to a method of preparing N-aryl piperazine with formula VI where Aryl is 4-cyanophenyl. Another preferred embodiment of the present invention is a process for making N1-(2'-pyridyl)-1,2-propanediamine sulfamic acid, a novel, easy to isolate solid intermediate for the preparation of N-aryl piperazines, and novel derivatives thereof which are also useful for the preparation of N-aryl piperazines.

Certain compounds in the processes of the present invention contain one asymmetric carbon atom, giving rise to enantiomeric forms of the compounds. It is to be understood that the invention encompasses the enantiomers thereof including racemic mixtures. Compounds possessing basic nitrogen can form complexes with many different acids (both protic and non-protic). The invention also includes acceptable salt forms formed from the addition reaction with either inorganic or organic acids. Inorganic acids such as hydrochloric acid (HCl), hydrobromic acid (HBr), hydroiodic acid (HI), sulfuric acid, phosphoric acid, nitric acid are useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid are useful.

In one preferred embodiment of this invention, a compound of formula IV where Ar is dihydrobenzodioxinyl is prepared by dialkylation of an aniline in the presence of excess chloroethanol followed by conversion of the resulting hydroxyl moiety to a suitable leaving group, e.g., Cl, Br, mesylate, or tosylate:

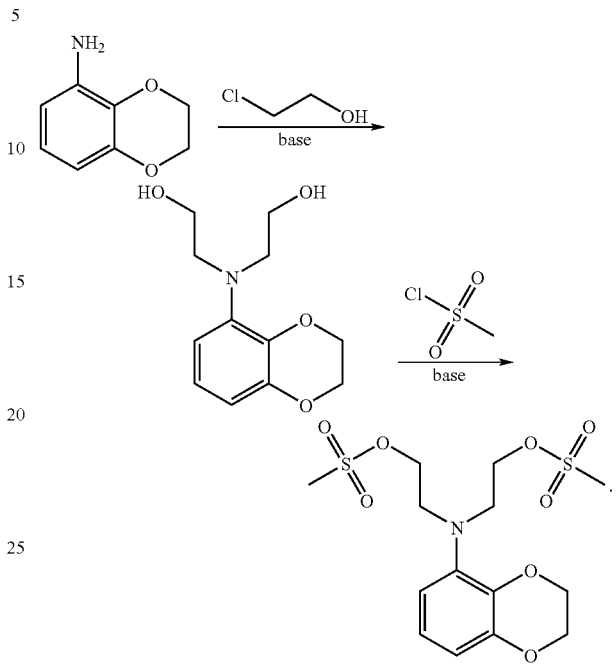

Alternatively, compound of formula IV where Ar is dihydrobenzodioxinyl is prepared by dialkylation of an aniline with alkyl haloacetate followed by reduction.

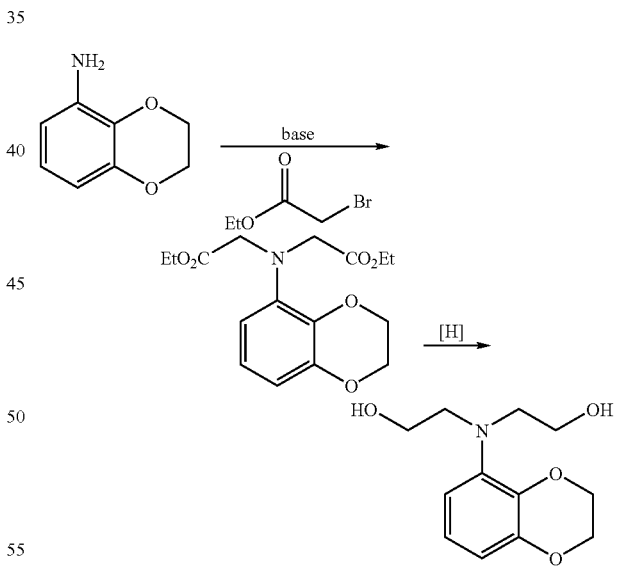

In a preferred embodiment of the present invention, a compound of formula I where R=$CH_3$ is opened with ammonia, with inversion of the stereocenter, to give N1-(2'-pyridyl)-1,2-propane-diamine sulfamic acid as an easily isolated solid. In other embodiments, the sulfamidate of formula I is opened with amines such as benzyl amine or benzhydryl amine to give the corresponding sulfamic acids. The resulting compound can then be hydrogenated under hydrogenation condition to give a sulfamic acid. One such embodiment is illustrated below:

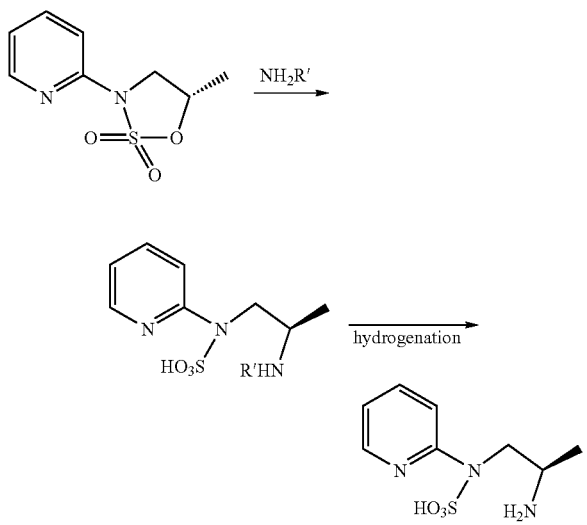

where R' is benzhydryl or benzyl.

In another preferred aspect of this invention, N1-(2'-pyridyl)-1,2-propanediamine sulfamic acid is coupled with a dimesylate to form a piperazine:

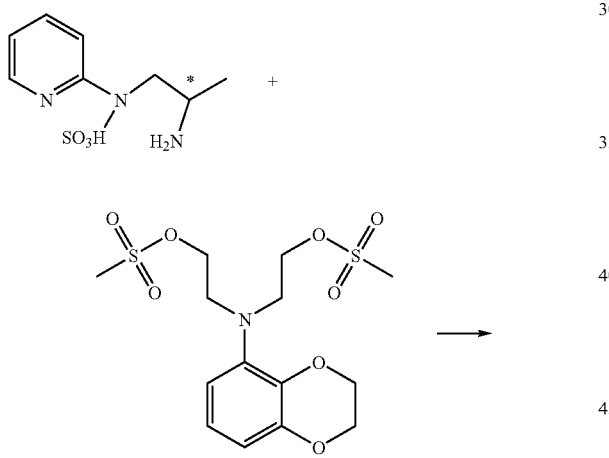

where * indicates an asymmetric carbon stereocenter.

The sulfamic acid moiety may also function as a protecting group in the coupling step with the dimesylate to form the piperazine. The chirality of the piperazine compound remains intact throughout the synthetic sequence.

This invention provides a process using N1-(2'pyridyl)-1,2-propane-diamine sulfamic acid that would be useful in the synthesis of optically active N, N'-disubstituted piperazines in a one-step, stereoselective and convergent manner. The optically active N.N'-disubstituted piperazines have activity as $5\text{-HT}_{1A}$ (serotonin) receptor antagonists.

In the compound of formula IV, L may be any suitable leaving group. Those skilled in the art will readily be able to determine which groups are suitable in the practice of the invention. Examples of such suitable leaving groups include chloro, bromo, mesylate, tosylate and p-bromophenylsulfonyloxy groups.

Where the presence of an acid, base, or solvent is needed in a reaction of the present invention, any suitable acid, base or solvent known in the art may be used. Those skilled in the art will readily be able to identify suitable solvents, acids and bases to use in the practice of this invention.

The following examples are presented to illustrate certain embodiments of the present invention, but should not be construed as limiting the scope of this invention. The reagents and solvents for the individual step are given for illustrative purposes only and may be replaced by reagents and solvents known to those skilled in the art.

EXAMPLE 1

Benzhydrylamine Opening of Sulfamidate

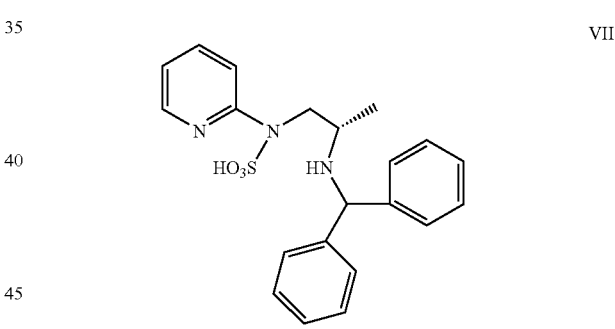

VII

To a solution of sulfamidate of formula I (R=methyl) (8.0 g, 37 mmol) in acetonitrile (64 mL), aminodiphenylmethane (8.1 g, 44 mmol) is added. The reaction mixture is stirred at ambient temperature under Ar for 2 days, then warmed to 55° C. for an additional 8 hours. The resulting suspension is filtered, washed with $Et_2O$ (40 mL) and air-dried to give 12 g (82%) of the above compound of formula VII as an off-white solid.

$R_f$=0.31 (10:1 $CHCl_3$:$CH_3OH$); $^1H$ NMR (DMSO) δ 9.77 (bs, 1H, OH), 7.15-8.0 (m, 13H), 6.7-6.8 (m, 1H), 5.81 (bs, 1H, NH), 4.1-4.3 (m, 2H), 3.4 (m, 2H), 1.3 (d, J=4.8 Hz, 2H); $^{13}C$ NMR (DMSO) δ 155.2, 146.5, 137.4, 136.4, 129.4, 129.3, 129.2, 129.0, 128.8, 128.1, 127.8, 127.7, 127.5, 127.5, 126.3, 116.0, 114.8, 62.4, 57.3, 53.2, 50.1, 14.4; IR (KBr): $\upsilon_{max}$ 3432, 3057, 3010, 2931, 2836, 2663, 2508, 2330, 1599, 1565, 1500, 1474, 1433 $cm^{-1}$; CHN (calculated) C 63.48 H 5.79 N 10.57, CHN (observed) C 63.38 H 5.74 N 10.52; MP=203.5-208° C.

EXAMPLE 2

Hydrogenation to Sulfamic Acid

VIII

A mixture of benzhydryl protected sulfamic acid of formula VII (5.0 g, 12 mmol), 10% Pd/C (2.1 g) in EtOH (100 mL) is stirred at ambient temperature under a balloon of H$_2$. After 2 days, the reaction mixture is filtered through a bed of celite, washed with hot EtOH (100 mL) and concentrated in vacuo to provide 1.98 g (72%) of the compound of formula VIII as an off-white solid. $^1$H NMR (DMSO) δ 8.17 (d, J=3 Hz, 1H), 7.5-7.9 (m, 5H), 6.82 (t, J=4.5 Hz, 1H), 4.03 (dd, J=10.8 Hz, 3.6 Hz, 1H), 3.94 (dd, J=10.8 Hz, 5.7 Hz, 1H), 3.4-3.6 (m, 1H) 1.18 (d, J=5.1 Hz, 3H); $^{13}$C NMR (DMSO) δ 156.1, 146.8, 136.9, 115.7, 114.6, 50.1, 47.9, 16.7; IR (KBr): υ$_{max}$ 3426, 3137, 3073, 2980, 2518, 1629, 1588, 1520, 1465, 1432, 1366, 1286, 1234, 1197, 1146, 1117, 1063, 1042 cm$^{-1}$; CHN (calculated) C 41.6 H 5.62 N 18.2, CHN (observed) C 41.1 H 5.49 N 17.7; MP=175.5-179° C.

EXAMPLE 3

Ammonia Opening of Sulfamidate

VIII

A mixture of sulfamidate of formula I (R=methyl) (22 g, 0.11 mol) in a 2 N ammonia in EtOH solution (216 mL, 0.432 mol) is stirred at ambient temperature under N$_2$ for 2 days. This mixture is then concentrated to ¼ its original volume. The mixture is filtered, washed with Et$_2$O (50 mL) and air-dried to give 17 g (72%) of sulfamic acid of formula VIII as an off-white solid.

EXAMPLE 4

Hydrolysis of Sulfamic Acid

IX

A solution of sulfamic acid of formula VIII (0.97 g, 4.2 mmol) in 3 N HCl (10 mL) is stirred at ambient temperature for 18 h. After this time, the reaction mixture is basified to pH 13-14 with 6 N NaOH (5 mL) and extracted with Et$_2$O (3×40 mL). The combined organic layers is dried over Na$_2$SO$_4$, filtered and concentrated in vacuo to give 0.49 g (78%) of N1-(2'-pyridyl)-1,2-propanediamine as a yellow oil. $^1$H NMR (CD$_3$OD) δ 7.8-8.0 (m, 2H), 7.3-7.5 (m, 2H), 6.5-6.7 (m, 2H), 3.0-3.4 (m, 3H).

EXAMPLE 5

Coupling of Sulfamic Acid and Dimesylate

X

XI

To a solution of dimesylate of formula X (30.5 g, 84 mmol) in anhydrous DMF (240 mL), are added sulfamic acid VIII (16.2 g, 70 mmol), potassium carbonate (31.0 g, 224 mmol) and lithium bromide (12.8 g, 147 mmol). The reaction mixture is heated in an 80-83° C. oil-bath for 18 h under N$_2$ then cooled to room temperature, and then poured into a mixture of 3 N HCl (400 mL) and CHCl$_3$ (200 mL). This mixture is stirred at ambient temperature for 1 h before the two layers are separated. The aqueous layer is washed with CHCl$_3$ (2×75 mL) to remove the less polar impurities, then basified to pH~14 with 5 N NaOH (250 mL). The basic aqueous layer is then extracted with CHCl$_3$ (3×150 mL). The combined organic layers are dried over Na$_2$SO$_4$, filtered, concentrated in vacuo to give 23 g (92%) of the compound of formula XI as a brown syrup.

EXAMPLE 6

Formation of A Piperazine Compound

To a solution of dimesylate of formula X (57 mg, 0.14 mmol) in anhydrous acetonitrile (1 mL) is added aminopyridine (20 mg, 0.13 mmol), potassium carbonate (52 mg, 0.38 mmol) and lithium bromide (26 mg, 0.30 mmol). The reaction mixture is heated to reflux for 15 h under N$_2$ then cooled to room temperature before filtering through a pad of celite. The pad is then washed with acetonitrile. The combined organic layers are dried over Na$_2$SO$_4$, filtered, and concentrated in vacuo to give 52 g (105%) of piperazine XI as a yellow oil (92% area % by GC/MS).

EXAMPLE 7

Formation of Piperazine Dihydrochloride

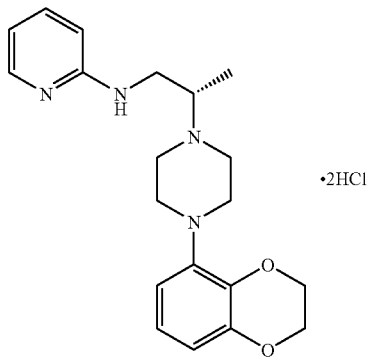

To piperazine XI (23 g, 65 mmol), a 1 M solution of HCl in EtOH (125 mL, 125 mmol) is added. This mixture is concentrated in vacuo, then redissolved in CH$_3$OH (25 mL). Et$_2$O (15 mL) is added slowly. After 18 h at ambient temperature, off-white solids form. The solid is filtered, washed with cold EtOH (5 mL) and air-dried to provide 4.6 g of the dihydrochloride of compound XI as an off-white solid. The mother liquor is set aside. After an additional 5 days, more solid forms. This is filtered, washed with cold EtOH (5 mL) and air-dried to give an additional 3.7 g of the dihydrochloride of compound XI as an off-white solid.

EXAMPLE 8

Acylation of A Piperazine Compound

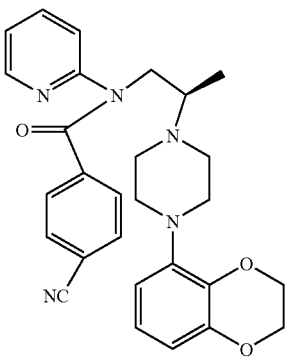

XII

To a solution of potassium carbonate (3.4 g, 24.6 mmol) in H$_2$O (5 mL), is added the dihydrochloride made in Example 7 (3.0 g, 7.0 mmol), followed by EtOAc (17 mL). The mixture is stirred in a 0-5° C. ice-bath for 15 min before the addition of 4-cyanobenzoyl chloride (1.3 g, 7.9 mmol) in EtOAc (3.5 mL) is added slowly. After 1 h, TLC indicates a small amount of starting material. Additional 4-cyanobenzoyl chloride (100 mg, 0.60 mmol) is added. After an additional 1 h, H$_2$O (10 mL) is added. The two layers are separated. The organic layer is extracted with a saturated NaCl solution (10 mL), H$_2$O (10 mL). The aqueous layers are back extracted with EtOAc (2×10 mL). The combined organic layers are dried over Na$_2$SO$_4$, filtered, concentrated in vacuo to give 3.0 g (88%) of the compound of formula XII as a yellow foam.

EXAMPLE 9

Alkylation of Benzodioxane Aniline to Diester

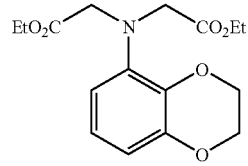

A mixture of benzodioxane aniline (3.0 g, 20 mmol), ethyl bromoacetate (7.5 mL, 68 mmol), Hunig's base (12.5 mL, 72 mmol) and NaI (0.3 g, 2.0 mmol) in toluene (30 mL) was heated to reflux. After 23 h, the reaction mixture was cooled to rt. Water (25 mL) was added. The two layers were separated. The aqueous layer was extracted with toluene (25 mL). The combined organic layers were dried over Na$_2$SO$_4$, filtered and concentrated in vacuo to give 6.5 g (100%) yield of the diester as brown oil. $^1$H NMR (CDCl$_3$) δ 6.70 (t, J=8.1 Hz, 1H), 6.3-6.6 (m, 2H), 4.1-4.3 (m, 12H), 1.2-1.3 (m, 6H).

EXAMPLE 10

Reduction of Benzodioxane Diester to Diol

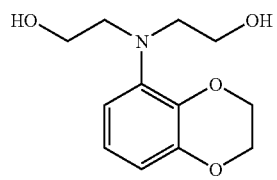

A mixture of diester (24 g, 74.3 mmol) in THF (240 mL) was cooled to 0-5° C. before LAH pallets (9.9 g, 260 mmol) were added slowly while maintaining reaction temperature below 10° C. After the addition of LAH, the cooling bath was removed and stirring was continued at rt overnight. After 18 h of stirring, the reaction mixture was cooled to 0±5° C. in dry ice/IPA bath. Water (10 mL) was added to reaction mixture slowly, followed by 15% aq, sodium hydroxide (10 mL) and water (30 mL). The resulted mixture was stirred for 30 min then filtered. The solids were washed with THF (100 ml). The filtrate was concentrated in vacuo to give 14.5 g (81%) of diol of formula IV as thick clear oil of 98 area % (LC-MS) purity. $^1$H NMR (CDCl$_3$) δ 6.88-6.70 (m, 3H), 4.34-4.22 (m, 4H), 3.54 (t, J=7.5Hz, 4H), 3.18 (t, J=7.5Hz, 4H).

EXAMPLE 11

Dialkylation of Benzodioxane Aniline to Diol

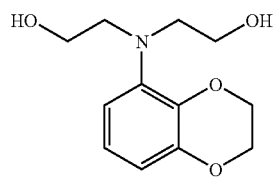

A mixture of benzodioxane aniline with 2-chloroethanol (210 mL, 3.1 mol) and Hunigs base (105 mL, 0.6 mol) was heated to 120° C. After 12.5 h, heating was stopped and allowed the reaction mixture to cool to rt. Ethyl acetate (300 mL) is added and the solution is washed with diluted brine (1×250 mL) followed by brine (2×75 mL). All aqueous layers are combined, the pH adjusted to 7 with $K_2CO_3$, and solution is back-washed with ethyl acetate (2×100 mL). All organic layers are then combined and extracted with 2N HCl (3×150 mL). The resulting aqueous solution is neutralized with solid $K_2CO_3$ to pH 7 and extracted with ethyl acetate (3×100 mL). The organic phase is dried with $MgSO_4$, concentrated and chased with toluene (2×50 mL) to remove residual chloroethanol to give 39.6 g (80%) of crude product as a dark oil of 94 area % (LC-MS) purity. $^1$H NMR (CDCl$_3$) δ 6.88-6.70 (m, 3H), 4.34-4.22 (m, 4H), 3.54 (t, J=7.5 Hz, 4H), 3.18 (t, J=7.5Hz, 4H).

Many variations of the present invention not illustrated herein will occur to those skilled in the art. The present invention is not limited to the embodiments illustrate and described herein, but encompasses all the subject matter within the scope of the appended claims and equivalents thereof.

What is claimed is:

1. A process for making a compound of the formula

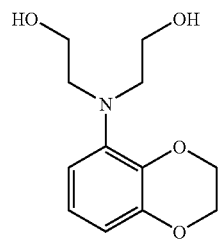

comprising dialkylating a benzodioxane aniline in the presence of chloroethanol.

2. The process of claim 1 wherein the chloroethanol is 2-chloroethanol.

3. A process for making a compound of the formula

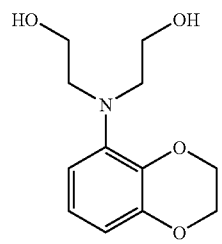

comprising dialkylating a benzodioxane aniline in the presence of alkyl haloacetate to produce a diester and reducing the diester to form a diol.

4. The process of claim 3 wherein the alkyl haloacetate is ethyl bromoacetate.

5. The process of claim 3 wherein the diester is reduced in the presence of LAH.

6. A process for making a compound of the formula

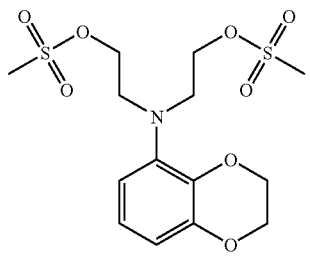

comprising dialkylating a benzodioxane aniline in the presence of chloroethanol to form a compound having the formula

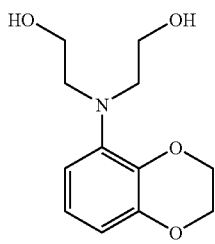

and converting the diol to mesylate groups to form a compound having the formula

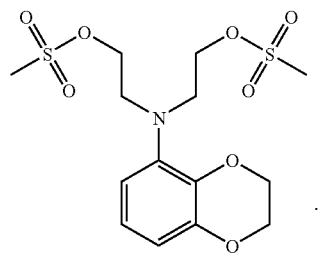

7. The process of claim 3 further comprising converting the diol to mesylate groups to form a compound having the formula

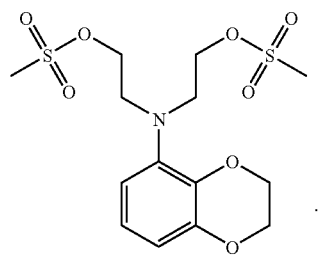

* * * * *